US011400073B2

(12) United States Patent
Petitjean

(10) Patent No.: US 11,400,073 B2
(45) Date of Patent: Aug. 2, 2022

(54) PREVENTION AND TREATMENT OF BENIGN PROSTATIC HYPERPLASIA USING A SELECTIVE INHIBITOR OF THE PRODUCTION OF REACTIVE OXYGEN SPECIES OF MITOCHONDRIAL ORIGIN

(71) Applicant: Olivier Petitjean, Senlis (FR)

(72) Inventor: Olivier Petitjean, Senlis (FR)

(73) Assignee: Olivier Petitjean, Senlis (FR)

( * ) Notice: Subject to any disclaimer, the term of this patent is extended or adjusted under 35 U.S.C. 154(b) by 106 days.

(21) Appl. No.: 16/650,303

(22) PCT Filed: Oct. 10, 2018

(86) PCT No.: PCT/FR2018/052509
§ 371 (c)(1),
(2) Date: Mar. 24, 2020

(87) PCT Pub. No.: WO2019/073173
PCT Pub. Date: Apr. 18, 2019

(65) Prior Publication Data
US 2020/0289461 A1 Sep. 17, 2020

(30) Foreign Application Priority Data
Oct. 11, 2017 (FR) .................................... 1759511

(51) Int. Cl.
*A61K 31/385* (2006.01)
*A61K 31/455* (2006.01)
*A61K 45/06* (2006.01)
*A61P 13/08* (2006.01)

(52) U.S. Cl.
CPC ............ *A61K 31/385* (2013.01); *A61P 13/08* (2018.01); *A61K 31/455* (2013.01); *A61K 45/06* (2013.01)

(58) Field of Classification Search
CPC .... A61K 31/385; A61K 31/455; A61K 45/06; A61P 13/08; C07D 339/02; C07D 339/04; C07D 339/06; C07D 339/00
See application file for complete search history.

(56) References Cited

U.S. PATENT DOCUMENTS

2013/0064904 A1* 3/2013 Gojon-Romanillos ..................... A61P 37/08
424/705

FOREIGN PATENT DOCUMENTS

| WO | 2009/037556 A1 | 3/2009 | |
| WO | WO-2009037556 A1 * | 3/2009 | ........... C07D 403/14 |
| WO | 2017/042267 A1 | 3/2017 | |
| WO | WO-2017042267 A1 * | 3/2017 | ........... A61K 31/385 |
| WO | WO-2017153220 A1 * | 9/2017 | ......... A61K 31/5355 |

OTHER PUBLICATIONS

Li et al. "Determination of anethole trithione in human plasma using high performance liquid chromatography coupled with tandem mass spectrometric detection" Analytics Chimica Acta 2007, 594, 274-278. (Year: 2007).*
Saito et al. "Prostatic ischemia induces ventral prostatic hyperplasia in the SHR; possible mechanism of development of BPH" Scientific Reports 2014, 4:3822, 1-7 (Year: 2014).*
Berger, A.P., et al., "Vascular resistance in the prostate evaluated by colour Doppler ultrasonography: is benign prostatic hyperplasia a vascular disease?," BJUI International, vol. 98, Aug. 2, 2006, pp. 587-590.
Bernichtein, S., "Anti-inflammatory properties of Lipidosterolic extract of *Serenoa repens* (Permixon®) in a mouse model of prostate hyperplasia," The Prostate, vol. 75, Issue 7, May 15, 2015, pp. 706-722.
Bernichtein, S., et al., "High Milk Consumption Does Not Affect Prostate Tumor Progression in Two Mouse Models of Benign and Neoplastic Lesions," PLOS One, vol. 10, No. 5, May 2015, pp. 1-20.
Bernichtein, S., et al., "Vitamin D3 Prevents Calcium-Induced Progression of Early-Stage Prostate Tumors by Conteracting TRPC6 and Calcium Sensing Rexeptor Upregulation," Cancer Research, vol. 77, No. 2, Jan. 15, 2017, pp. 355-365.
Bjelakovic et al., Mortality in Randomized Trials of Antioxidant Supplements for Primary and Secondary Prevention Systematic Review and Meta-analysis, JAMA., (2007), vol. 297, No. 8,pp. 842-857.
Briganti, A., et al., "Benign Prostatic Hyperplasia and Its Aetiologies," European Association of Urology, vol. 8, Issue 13, Dec. 2009, pp. 865-871.
Chou, P-S., et al., "Increased Risk of Benign Prostate Hyperplasia in Sleep Apnea Patients: A Nationwide Population-Based Study," PLOS One, vol. 9, Issue 3, Mar. 25, 2014, pp. 1-7.
Fibbi, B., "Chronic inflammation in the pathogenesis of benign prostatic hyperplasia," International Journal of Andrology, vol. 33, Issue 3, Jun. 1, 2010, pp. 475-488.
Fox, P.C., "Salivary Enhancement Therapies," Caries Research, vol. 38, No. 3, Jan. 1, 2004, pp. 241-246.
Goodman et al., The Beta-Carotene and Retinol Efficacy Trial Incidence of Lung Cancer and Cardiovascular Disease Mortality During 6-Year Follow-up After Stopping—Carotene and Retinol Supplements, Journal of the National Cancer Institute, vol. 96, No. 23, (Dec. 2004), pp. 1743-1750.
Gu, N-Y., et al., "Trichomonas vaginalis induces IL-1β production in a human prostate epithelial cell line by activating the NLRP3 inflammasome via reactive oxygen species and potassium ion efflux," The Prostate, vol. 76, No. 10, Jul. 2016, pp. 885-896.
Han, H., et al., "Signalling pathways associated with IL-6 production and epithelial-mesenchymal transition induction in prostate epithelial cells stimulated with Trichomonas vaginalis," Parasite Immunology, vol. 38, No. 11, Nov. 1, 2016, pp. 678-687.
International Search Report for International Application No. PCT/FR2018/052509, dated Jan. 9, 2019, 3 pages.

(Continued)

Primary Examiner — Amanda L. Aguirre
(74) Attorney, Agent, or Firm — TraskBritt

(57) ABSTRACT

A method of preventing and/or treating disease in which reactive oxygen species (or ROSs) of mitochondrial origin are involved. The method involves use of an inhibitor of mitochondrial ROS production, in particular, of anethole trithione, for the prevention and/or treatment of benign prostatic hyperplasia.

18 Claims, 13 Drawing Sheets

(56) References Cited

OTHER PUBLICATIONS

International Written Opinion for International Application No. PCT/FR2018/052509, dated Jan. 9, 2019, 7 pages.
Khandrika, L., et al., "Role of Oxidative Stress in Prostate Cancer," Cancer Letter, vol. 282, No. 2, Sep. 2018, pp. 125-136.
Kim, H-J, et al., "Pathogenic role of HIF-1a in prostate hyperplasia in the presence of chronic inflammation," Biochimica et Biophysica Acta, vol. 1832, No. 1, Jan. 2013, pp. 183-194.
Kim, J-H., et al., "Proliferation of Prostate Stromal Cell Induced by Benign Prostatic Hyperplasia Epithelial Cell Stimulated With Trichomonas vaginalis via Crosstalk With Mast Cell," Prostate, vol. 76, No. 15, Nov. 2016, pp. 1431-1444.
Kim, S-S., et al., "Inflammatory Responses in a Benign Prostatic Hyperplasia Epithelial Cell Line (BPH-1) Infected with Trichomonas vaginalis," Korean J Parasitol, vol. 54, No. 2, Apr. 2016, pp. 123-132.
Kindblom, J., et al., "Prostate Hyperplasia in a Transgenic Mouse with Prostate-Specific Expression of Prolactin," Endocrinology, vol. 144, No. 6, Jul. 2003, pp. 2269-2278.
Kumar, H., et al., "Hypoxia Inducible Factor Pathway and Physiological Adaptation: A Cell Survival Pathway?," Hindawi Publishing Corporation Mediators of Inflammation, vol. 2015 (accepted Dec. 2014), Article ID 584758, pp. 1-11.
Lakatta, E.G., "Arterial and Cardiac Aging: Major Shareholders in Cardiovascular Disease Enterprises," Part III: Cellular and Molecular Clues to Heart and Arterial Aging, Clinical Cardiology: New Frontiers, Circulation, vol. 107, No. 3, Jan. 28, 2003, pp. 490-497.
Lappas, M., et al., "The anti-inflammatory and antioxidative effects of nicotinamide, a vitamin B3 derivative, are elicited by FoxO3 in human gestational tissues: implications for preterm birth," The Journal of Nutritional Biochemistry, vol. 22, Issue 12, Dec. 2011, pp. 1195-1201 (Abstract).
Li et al., "HPLC determination of 4-hydroxy-anethole trithione in plasma via enzymatic hydrolysis and its application to bioequivalence study," Journal of Pharmaceutical and Biomedical Analysis, vol. 47, Issue 3, Jul. 15, 2008, pp. 612-617 (abstract only).
Meneses, A., et al., "PHD2: from hypoxia regulation to disease progression," Hypoxia (Auckl), vol. 4, Apr. 11, 2016, pp. 53-67.
Minciullo, P.L., et al., "Oxidative Stress in Benign Prostatic Hyperplasia: A Systematic Review," Urologia Internationalis, vol. 94, Dec. 5, 2014, pp. 249-254.
Navarrete, R.V, et al., "BPH and inflammation: pharmacological effects of Permixon on histological and molecular inflammatory markers. Results of a double blind pilot clinical assay," European Urology, vol. 44, No. 5, Nov. 2003, pp. 549-555 (Abstract).
Nunzio, C.D., et al., "Inflammatory mediators in the development and progression of benign prostatic hyperplasia," Nature Reviews Urology, vol. 13, Sep. 30, 2016, pp. 613-626 (Abstract).
Orr, A.L., et al., "Inhibitors of ROS production by the ubiquinonebinding site of mitochondrial complex I identified by chemical screening," Free Radical Biology and Medicine, vol. 65, Dec. 2013, pp. 1047-1059.
Ran, H., et al., "The effects of ROS in prostatic stromal cells under hypo environment," The Aging Male, vol. 18, Issue 2, Mar. 9, 2015, pp. 84-88.
Robert, G., et al., "Inflammation in benign prostatic hyperplasia: a 282 patients' immunohistochemical analysis," Prostate, vol. 69, No. 16, Dec. 2009, pp. 1774-1780.
Saito, M., et al., "Prostatic ischemia induces ventral prostatic hyperplasia in the SHR; possible mechanism of development of BPH," Scientific Reports, vol. 4, No. 1, Jan. 22, 2014, pp. 1-7.
Sala, L.S., et al., "A rare castration-resistant progenitor cell population is highly enriched in Pten-null prostate tumours," Journal of Pathology, vol. 243, Jul. 28, 2017, pp. 51-64.
Schramm, A., "Targeting NADPH oxidases in vascular pharmacology," Vascular Pharmacology, vol. 56, No. 5-6, May-Jun. 2012, pp. 216-231.
Seo, M-Y., et al., "Inflammatory response of prostate epithelial cells to stimulation by Trichomonas vaginalis," Prostate vol. 74, No. 4, Apr. 2014, pp. 441-449.
Sibert, L., et al., "Chronic pelvic pain: epidemiology and economic impact," Progrès en Urologie, vol. 20, No. 12, Sep. 29, 2010, pp. 872-885 (Abstract).
Silverio, F. D., et al., "Distribution of Inflammation, Pre-Malignant Lesions, Incidental Carcinoma in Histologically Confirmed Benign Prostatic Hyperplasia: A Retrospective Analysis," European Urology, vol. 43, Issue 2, Feb. 1, 2003, pp. 164-175 (Abstract).
Srivastava, D.S.L., et al., "Free Radical Injury and Antioxidant Status in Patients With Benign Prostate Hyperplasia and Prostate Cancer," Indian Journal of Clinica Biochemistry, vol. 20, 2, Jul. 2005, pp. 162-165.
Williams, P. A., et al., "Vitamin B3 modulates mitochondrial vulnerability and prevents glaucoma in aged mice," Science, vol. 355, No. 6326, Feb. 17, 2017pp. 756-760.
Wu, F., et al., "Elevated expression of HIF-Ia in actively growing prostate tissues is associated with clinical features of benign prostatic hyperplasia," Oncotarget, vol. 7, No. 11, Feb. 23, 2016, pp. 12053-12062.
Wu, X., et al., "The anti-hyperplasia, anti-oxidative and anti-inflammatory properties of Qing Ye Dan and swertiamarin in testosterone-induced benign prostatic hyperplasia in rats," Toxicology Letter, vol. 265, Jan. 4, 2017, pp. 9-16 (Abstract).
Yang, S.J., "Nicotinamide improves glucose metabolism and affects the hepatic NAD-sirtuin pathway in a rodent model of obesity and type 2 diabetes," The Journal of Nutritional Biochemistry, vol. 25, No. 1, Jan. 2014, pp. 66-72 (Abstract).

\* cited by examiner

PREVENTION AND TREATMENT OF BENIGN PROSTATIC HYPERPLASIA USING A SELECTIVE INHIBITOR OF THE PRODUCTION OF REACTIVE OXYGEN SPECIES OF MITOCHONDRIAL ORIGIN

CROSS-REFERENCE TO RELATED APPLICATIONS

This application is a national phase entry under 35 U.S.C. § 371 of International Patent Application PCT/FR2018/052509, filed Oct. 10, 2018, designating the United States of America and published as International Patent Publication WO 2019/073173 A1 on Apr. 18, 2019, which claims the benefit under Article 8 of the Patent Cooperation Treaty to French Patent Application Serial No. 17/59511, filed Oct. 11, 2017.

TECHNICAL FIELD

The present disclosure concerns the prevention and/or treatment of diseases in which reactive oxygen species (or ROSs) of mitochondrial origin are involved. It relates more particularly to the use of an inhibitor of mitochondrial ROS production, in particular, of anethole trithione, for the prevention and/or treatment of benign prostatic hyperplasia (BPH).

BACKGROUND

Benign Prostatic Hyperplasia

Chronic prostatitis, from which very many BPHs originate (Di Silvero F. et al., Eur Urol, 2003, 43: 164-175; Robert G. et al., Prostate, 2009, 69: 1774-1780), at least those that are not solely linked to aging, may be symptomatic or asymptomatic, bacterial or viral, of environmental or anatomical origin, and accompanied or otherwise by an increase in prostate-specific antigens (PSAs). It is commonly recognized nowadays that one third of men in the general population will present symptoms compatible with prostatitis over their lifetimes (Siber L. et al., Prog Urol, 2010, 20: 872-885). To this should be added all the cases of inflammatory, asymptomatic prostatitises that may be detected in specific instances by an ultrasound exam or that will remain unidentified if never searched for, particularly if the PSAs remain normal. BPH is found from the age of 35-40 years, and the prevalence thereof increases with age, reaching 75% in subjects over 50 years (Briganti A. et al., Eur Urol Suppl, 2009, 8: 865-871), with some cases remaining asymptomatic.

BPH is a chronic, progressive disease, the histological expression of which is characterized by abnormal development of the epithelial tissues and the fibromuscular stroma, principally in the anteromedial transition zones, but also in the peri-urethral zone. This tissue remodeling, with stromal hypertrophy and epithelial thickening, is the result of an imbalance between cell proliferation and apoptosis, regulated by hyperproduction of ROSs and overexpression of pro-inflammatory cytokines (Kim H-J. et al., Biochim Biophys Acta, 2013, 1832: 183-194; Miniciullo P L. et al., Urol Int, 2015, 94: 249-254; Saito M. et al., Sci Rep, 2014, 4: 3822). In fact, recent studies have shown that the local hypoxia created by the fall in local flow rates (Saito, 2014; Berger A P. et al., BJU Int, 2006, 98: 587-590), ischemia (Chou P S. et al., PLoS One, 2014, 9: e93081) and inflammation (Vela Navarrete R. et al., Eur Urol, 2003, 44: 549-555; Fibbi B. et al., Int J Androl, 2010, 33: 475-488) play a major role in the development and evolution of this disease, and ROSs are the pivotal element linking them (Ren H. et al., Aging Male, 2015, Early Online: 1-5 [9 Mar. 2015]; Saito, 2014).

The stromal cells that ordinarily form 40% of the glandular mass form the bulk of the prostatic tissue in the event of BPH. Their ROS, HIF1α and IL-8 content is considerably increased; this increase is enhanced in the case of hypoxia, and is accompanied by considerable cell proliferation (Ren, 2015). Vascular aging is itself a source of local ischemia (Lakatta E G., Circulation, 2003, 107: 490-497) and hypoxia; Wu further shows that in 70% of cases, BPH is associated with tissue hypoxia, with prostatic HIF1α levels that, in humans, are linked to the intra-acinar weight of the prostate (Wu F. et al., Oncotarget, 2016, 7: 12053-12062). The response to this chronic hypoxia begins with the activation of HIFs (hypoxia-inducible factors), since the HIF pathway is the primary cell regulation pathway in response to a lack of 02 (Kumar H. and Choi D-K, Mediators of inflammation, 2015, ID 584758, Hindawi Publish Corp.; Meneses A M. and Wielockx B., Hypoxia, 2016, 4: 53-67). HIFs, for which 3 isoforms are known (HIF1a, 2a and 3a), are therefore heterodimers responsible for coordinating transcriptional cell responses to hypoxia. HIFs consist of an a protein, or HIFα, which is solely induced by hypoxia, and a P protein, or ARNT (arylhydrocarbon receptor nuclear translocator), which is constitutively expressed.

In normoxia, the a fraction is broken down as it is produced. It is PHDs (propylhydroxylase domain enzymes), a family of dioxygenases consisting of 3 isoforms ($PHD_{1-3}$), i.e., oxidases, that give the instruction for the breakdown of HIF-1α, being in a manner of speaking a sensor of hypoxia. For this purpose, the PHDs are covalently bonded to the ODD domains (oxygen-dependent degradation domains) of the HIF-α's; the hydroxylase activity thus developed is modulated by the mtROSs, which are in effect inhibitors of the PHDs. Their action is facilitated by the fact that, in a case of moderate hypoxia, the production of ROSs by the mitochondrion is, paradoxically, overexpressed (Kumar, 2015). The inhibition of the mitochondrial complex 1, like the inflow of ROS scavengers (free radical scavengers), also blocks the stabilization of HIF-1α induced by hypoxia (Kumar, 2015). For Kumar (2015), the production of mtROSs is the element responsible for the cell propagation of the "hypoxia" signal.

The ROSs will act as a second messenger, activating a multitude of cell signaling pathways, and thus facilitate the action of the growth factors that will promote the cellular proliferation, of the cytokines, of NF-κB (which is a ROS inducer and a pro-proliferation, anti-apoptotic and pro-inflammatory element), and of some chemokines. It should be added that the hyperproduction of HIF-1α contributes to the stimulation of the epithelial-mesenchymal transition, which is a powerful cellular mobility factor that also takes part in the aforementioned tissue remodeling (Kim, 2013; Wu X. et al., Toxicol Lett, 2017, 265: 9-16).

In the context of hyperproduction of free radicals, ROSs and mtROSs (in which the production of one stimulates the production of the other so as to form a full-fledged amplification system by reciprocal oxidation [Schramm A. et al., Vascul Pharmacol, 2012, 56: 216-231]), the cellular antioxidants are rapidly consumed, and are not present in the cell to combat the excess of the ROSs that are thus produced (Khandrika L. et al., Cancer Lett, 2009, 282: 125-136; Srivastava D S. and Mittal R D. Indian J Clin Biochem, 2005, 20: 162-165).

Finally, the inflammation itself stimulates the expression of HIF-1α via different cytokines produced by the stromal cells and by the immune cells that infiltrate the inflammatory zones (Kim, 2013; Saito, 2014). In this regard, it should be emphasized that any prostatic infection is responsible for an inflammatory reaction, which will be accompanied locally by hyperproduction of ROSs and by up-regulation of NF-κB and of pro-inflammatory cytokines (IL-1β, -6, -8) (Gu N-Y. et al., Prostate, 2016, 76: 885-896; Han I H. et al., Parasite Immunol, 2016, 38: 678-687; Kim S-S. et al., Korean J Parasitol, 2016, 54: 123-132; Seo M-Y. et al., Prostate, 2014, 74: 441-449); these inflammation mediators, released by the epithelial cells in response to an infection, induce the migration and activation of the mastocyte cells, causing proliferation of the stromal cells via the CXCL8-CXCR1 and CCL2-CCR2 signaling pathways (Kim J H. et al., Prostate, 2016, 76: 1431-1444) and increases the invasive power thereof by promoting the epithelial-mesenchymal transition (EMT), an essential element of tissue remodeling (Han, 2016).

The Mitochondrion and ROS Production

The mitochondrion is involved in the pathogenesis of nearly all diseases associated with aging, including cardiovascular diseases, neurodegenerative diseases (Parkinson's disease, Alzheimer's disease, etc.), diabetes, as well as tissue dysfunctions of ischemic origin. It is widely acknowledged that it plays a central role in the free radical theory of aging. This theory states that the accumulation of damage caused by reactive oxygen species (ROSs) affects numerous cell functions, in particular, mitochondrial functions, which are essential for energy provision and good cell functionality. The mitochondria therefore appear to be the primary targets of ROSs, since optimal cell functionality is crucial for providing the energy that a cell needs to repair itself.

As well as being the primary generative source of ROSs, mitochondria are also particularly sensitive to damage caused by these ROSs. As a result, the mitochondria themselves generate the ROSs that are at the origin of the oxidation damage that contributes to cell dysfunction and death.

Numerous studies have been performed to evaluate the ability of antioxidants to counteract the effect of ROSs. Several antioxidant molecules have proven satisfactory in preclinical studies, but their effectiveness has been only partially confirmed in most clinical trials (Orr et al., 2013, Free Radic Biol. Med, 65: 1047-59).

Moreover, recent studies have shown that an excessive reduction in ROSs has a deleterious effect on cells, suggesting that balanced production of ROSs contributes to good cell functionality (Goodman et al., 2004 Dec. 1. *J. Natl. Cancer Inst.* 96(23): 1743-50; Bjelakovic G et al., 2007 Feb. 28. *JAMA.* 297(8):842-57).

BRIEF SUMMARY

Studies on the role of oxidative stress in numerous pathologies have demonstrated the benefit of having access to a selective inhibitor of mitochondrial ROS production. Currently available antioxidants do not have this specificity, resulting in a risk of side effects occurring when cytosolic ROS production is affected; these side effects have been described in detail.

The role of ROSs in BPH has already been underscored. On the one hand, in experimental *T. vaginalis* prostatic infection models, the inhibition of ROS production by an antiNOX2 (DPI: diphenylene iodonium) prevents overexpression of all the aforementioned cytokines, strongly suggesting that ROSs are at the origin of this overexpression (Kim S-S., 2016) and that this therapeutic approach is conceivable given the aim of preventing BPH development after infective prostatitis. On the other hand, recent studies show that treatment with edaravone, a non-specific ROS scavenger, decreases levels of prostatic ROSs, of HIF-1α and of VEGF and reduces cell proliferation, and ultimately promotes apoptosis, thus reestablishing the normal balance between proliferation and apoptosis (Ren, 2015). Considered as a whole, these results suggest the central role of ROSs in BPH.

In light of these observations, the inventors propose to reduce ROS production specifically at the mitochondrial level, to promote the preventative effect for the cell without experiencing the deleterious side effects of non-selective antioxidants. Thus, the inventors have established the benefit of administering a specific inhibitor of mitochondrial ROS production, in particular, anethole trithione (ATT), for the prevention and/or treatment of BPH.

In particular, the inventors have unexpectedly shown that ATT, unlike conventional antioxidants, acts directly and selectively on mitochondrial ROS production, mostly at the $I_Q$ site of the I complex of the mitochondrial respiratory chain, this site being both the principal ROS production site and the principal site of mitochondrial dysfunctions.

Furthermore, the inventors have preliminarily demonstrated that ATT does not affect mitochondrial oxidative phosphorylation, suggesting an absence of undesirable side effects and a possibility of treating and/or preventing diseases associated with free radicals of oxygen in the long term using this molecule. This property is of particular interest.

Finally, the inventors have now shown, in a murine benign prostatic hyperplasia model, that administering ATT reduces the androgenic signal while reducing prostatic inflammation. These preclinical results are quite satisfactory and highly promising for use in benign prostatic hyperplasia patients.

ATT already benefits from a market authorization under the trade name of SULFARLEM®, for increasing bile and saliva secretion. It is used for treating digestive difficulties and dry mouth. Thus, no side effect has been reported so far associated to long-term use of this molecule. ATT is thus the first drug for human use authorized by the FDA and EMA that prevents mitochondria from producing ROSs at the $I_Q$ site.

The present disclosure proposes, in a quite surprising and innovative manner, to use this drug in a new therapeutic indication, namely for the prevention and treatment of BPH.

DETAILED DESCRIPTION

Figure 1A:
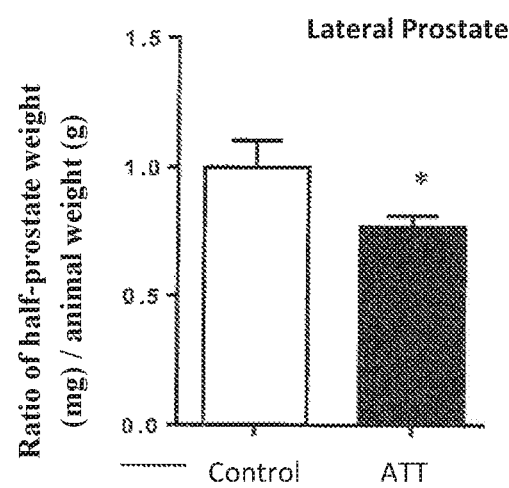
FIG. 1A shows the ratio between the weight of the lateral prostate (in mg) and the weight of the animal (in g) for the control group and the ATT group.

A first subject matter of the present disclosure relates to the use of a specific inhibitor of mitochondrial ROS production, in particular, anethole trithione (ATT), for the prevention and/or treatment of BPH.

A "specific inhibitor of mitochondrial ROS production" is understood to be any compound capable of specifically inhibiting ROS production at the mitochondrial respiratory chain without affecting the cellular ROS production at the cytosol; this specificity is paramount because it prevents the side effects associated with a lack of ROS at the cytosol, in particular, in the event of excessive inhibition of ROS production by a non-selective antioxidant. In a preferred embodiment, this inhibitor is capable of inducing specific inhibition of ROS production at the $I_Q$ site of the mitochondrial respiratory chain.

Inhibitors of this type are, for example, ATT, ATX or NC-POBS, although any other compound having the same specificity of inhibition is appropriate.

In a preferred embodiment, the specific inhibitor of mitochondrial ROS used for the prevention and/or treatment of BPH is ATT.

Within the meaning of the present disclosure, the use of an "inhibitor" is understood to be the use of at least one specific inhibitor of mitochondrial ROS production; this may therefore be one inhibitor or a combination of a plurality inhibitors, as is described hereinafter.

ATT, anethole trithione, is a 5-(4-methoxyphenyl)-3H-1,2-dithiole-3-thione. It is also known as AOL. It has the following formula:

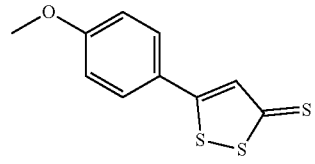

ATX corresponds to the phenolic form of ATT as metabolized by the liver, both in humans and in animals. This 4-OH-anethole trithione form has been described before (Li et al., J Pharm Biomed Anal, 2008, 47: 612-617). Since the structure of ATT is preserved during this metabolization, there is reason to suppose that the anti-ROS activity brought about by ATT is found in ATX, especially because after oral administration, which is currently the form on the market, the main part of the circulating product found is ATX (Yu, 2011). Moreover, ATX carries a para phenol group, which allows the formation of esters. In one particular embodiment, ATX is used in esterified form, for example, in the form of phosphate, ethylidenephosphate, sulfate, hemisuccinate, acetate, propionate, isobutyrate, hexanoate, pivaloate, ethoxycarbonate, or nicotinate ester, or even of the ester of amino acids such as glycine, diethylglycine or valine ester, and this list is non-limiting.

NC-POBS corresponds to N-cyclohexyl-4-(4-nitrophenoxy)benzenesulfonamide, the only molecule described in the literature thus far as a specific inhibitor of mitochondrial ROS production at the $I_Q$ site of the respiratory chain (Orr et al., 2013, Free Radic. Biol. Med., 65: 1047-1059).

In a preferred embodiment, the specific inhibitor is selected from ATT, ATX or an ATX ester. It is particularly preferred for the specific inhibitor to be ATT. In a particular embodiment, the prevention and/or treatment of BPH is achieved as a result of the combination of at least two molecules among ATT, ATX and an ATX ester.

Within the meaning of the present disclosure, "prevention" is understood to be the avoidance of the development of stromal hyperplasia and/or epithelial thickening in the anteromedial transition zones and the peri-urethral zones in a subject who is asymptomatic but likely to develop BPH. Subjects likely to develop BPH are, in particular, patients with chronic prostatitis.

Within the meaning of the present disclosure, "treatment" is understood to be a reduction in the symptoms associated with BPH, in particular, stabilization, regression or slowing of the appearance of stromal hyperplasia and/or epithelial thickening in the anteromedial transition zones and the peri-urethral zones in a subject affected by BPH. In the broadest sense, the term "treatment" also includes preventing the occurrence of BPH. The subject to be treated may be a human or an animal.

So far, among the treatments available for patients exhibiting symptoms associated with BPH, alpha blockers are predominant, ahead of 5-alpha-reductase inhibitors and phytotherapy. However, these treatments are partially effective and/or have long-term side effects.

Chronic prostatitis is thought to be at the origin of many BPHs. However, when it is of bacterial origin, chronic prostatitis may be resistant to antibiotic treatments: there is thus no alternative treatment. In this case, as in other chronic prostatitis cases, the inventors propose preventing the appearance of BPH by administering a specific inhibitor of mitochondrial ROS production, starting from the age of 30 or 40 years.

Thus, in a first particular embodiment, the present disclosure involves preventing the occurrence of BPH following chronic prostatitis.

As is set out in the introduction, the occurrence of BPH results from a combination of multiple factors, the central element of which is ROSs. In this context, administering a specific inhibitor of the production of mitochondrial ROS could, in its own right, enable etiological treatment of a recent BPH.

Within the meaning of the present disclosure, "recent BPH" is understood to be BPH that has been diagnosed recently. In practice, a patient will come for a consultation when the first clinical signs become troublesome. Management can be considered as soon as the diagnosis is made. However, implementation of symptomatic treatment is often delayed because the currently available drugs (alpha blocker and 5-alpha-reductase inhibitor) have long-term side effects. It would therefore be of great interest to have access to an alternative treatment without side effects. According to the inventors' hypotheses, this benefit could be achieved by administering an inhibitor of mitochondrial ROS production, such as ATT. The expected beneficial effects can range from slowing of the development of BPH, or stabilization of the disease, through to potential regression of the symptoms due to the inhibition of mitochondrial ROSs at an early stage of hyperplasia.

Thus, in a second particular embodiment, the present disclosure involves treating BPH in monotherapy by administering a specific inhibitor of mitochondrial ROS production, this inhibitor preferably being selected from ATT, ATX or an ATX ester or the combination of at least two of these molecules. This embodiment more particularly addresses recent BPH.

In a preferred embodiment, the present disclosure involves treating BPH in monotherapy, by administering anethole trithione (ATT).

When the treatment of BPH starts after the symptoms have set in, or when control over the symptoms has already started to be gained using alpha blockers, the specific inhibitor of mitochondrial ROS production can be combined with an alpha blocker. Currently available alpha blockers include alfuzosin, terazosin, tamsulosin and prazosin.

Thus, in a third particular embodiment, the present disclosure involves treating BPH by administering a specific inhibitor of mitochondrial ROS production, this inhibitor preferably being selected from ATT, ATX or an ATX ester or the combination of at least two of these molecules, in combination with an alpha blocker.

In a preferred embodiment, the present disclosure involves treating BPH by administering anethole trithione (ATT) in combination with an alpha blocker.

Likewise, when the treatment of BPH starts after the symptoms have set in, or when control over the symptoms has already started to be gained using 5-alpha-reductase, the specific inhibitor of mitochondrial ROS production can be combined with a 5-alpha-reductase inhibitor. Currently available 5-alpha-reductase inhibitors include finasteride, a selective inhibitor of type II 5-alpha-reductase, and dutasteride, an inhibitor of both type I and type II iso-enzymes.

In a preferred embodiment, the present disclosure involves treating BPH by administering anethole trithione (ATT) in combination with a 5-alpha-reductase inhibitor.

In a fourth particular embodiment, the present disclosure involves treating BPH by administering a specific inhibitor of mitochondrial ROS production, this inhibitor preferably being selected from ATT, ATX or an ATX ester or the combination of at least two of these molecules, in combination with a 5-alpha-reductase inhibitor.

In a preferred embodiment, the present disclosure involves treating BPH by administering anethole trithione (ATT) in combination with nicotinamide.

In addition, the combination with nicotinamide, a molecule that induces cellular antioxidant enzymes such as SOD, GPX, catalase and inhibits production of the three pro-inflammatory cytokines TNFα, IL-6 and IL-8, is conceivable (Lappas M. and Permezel M., J Nutr Biochem, 2011, 22: 1195-1201; Yang S J., J Nutr Biochem, 2014, 25: 66-72), especially as BPH is an aging pathology and it is specifically nicotinamide levels that decrease with age (Williams P A. et al., Science, 2017, 355: 756-760).

In a fifth embodiment, the present disclosure involves treating BPH by administering a specific inhibitor of mitochondrial ROS production, this inhibitor preferably being selected from ATT, ATX or an ATX ester or the combination of at least two of these molecules, in combination with nicotinamide. In a variant of the present disclosure, the BPH treatment is achieved by administering (i) a specific inhibitor of mitochondrial ROS production selected from ATT, ATX or an ATX ester or the combination of at least two of these molecules, (ii) nicotinamide and (iii) an alpha blocker. In an alternative embodiment, the present disclosure involves treating BPH by administering anethole trithione (ATT) in combination with nicotinamide and an alpha blocker.

In another variant of the present disclosure, the BPH treatment is achieved by administering (i) a specific inhibitor of mitochondrial ROS production selected from ATT, ATX or an ATX ester or the combination of at least two of these molecules, (ii) nicotinamide and (iii) a 5-alpha-reductase inhibitor.

In another alternative embodiment, the present disclosure involves treating BPH by administering anethole trithione (ATT) in combination with nicotinamide and a 5-alpha-reductase inhibitor.

The present disclosure also relates to a method for treating BPH involving administering a therapeutically effective dose of a specific inhibitor of mitochondrial ROS production to a patient who requires it.

A second subject matter of the present disclosure relates to the use of a specific inhibitor of mitochondrial ROS production for reducing the prostatic androgenic signal. This use is applicable, in particular, to BPH treatment.

In a preferred embodiment, the present disclosure relates to the use of anethole trithione (ATT) for reducing the prostatic androgenic signal.

This use is compatible with the therapeutic benefit achieved by virtue of 5-alpha-reductase inhibitors, which are the molecules currently most used in BPH treatment.

This effect of ATT is supported by the results presented in the examples below, in particular, in paragraph 3, in relation to FIGS. 3A to 6C, which show a visible anti-androgenic effect on the androgen receptors, the 5-alpha-reductase 1 and 2 receptors (which serve to transform testosterone into its active metabolite, dihydrotestosterone), and the PSP94 receptors (target gene activated via the androgenic pathway).

A third subject matter of the present disclosure relates to the use of a specific inhibitor of mitochondrial ROS production for reducing prostatic inflammation. This use is applicable, in particular, to the treatment of prostatitises and BPH.

In a preferred embodiment, the present disclosure relates to the use of anethole trithione (ATT) for reducing prostatic inflammation.

The effect of inflammation in promoting the progression of benign prostatic hypertrophy is increasingly recognized, and so inhibition of prostatic inflammation is particularly desirable in the treatment of BPH (De Nunzio et al., 2016).

This effect of ATT is supported by the results presented in the examples below, in particular, in paragraph 4, in relation to FIGS. 7 to 9C, which show a visible anti-inflammatory effect through the reduction in CD45 marker, as well as the reduction in IL6 and TNFalpha pro-inflammatory markers.

In a preferred embodiment, the present disclosure involves the use of a specific inhibitor of mitochondrial ROS production for simultaneously reducing the prostatic androgenic signal and prostatic inflammation.

In an even more preferred embodiment, the present disclosure involves the use of anethole trithione (ATT) for simultaneously reducing the prostatic androgenic signal and prostatic inflammation.

On the basis of the treatments available thus far, it is acknowledged that there is an inverse relationship between intra-prostatic inflammation and the androgenic signal, visible, in particular, when the androgenic signal is experimentally reduced (for example, castration), leading to an increase in the inflammation.

However, quite surprisingly, the inventors have now shown that the use of a specific inhibitor of mitochondrial ROS production, such as anethole trithione, leads to a reduction in the androgenic signal accompanying a reduction in intra-prostatic inflammation. An action mechanism of this type is completely original, and particularly suited to the treatment of benign prostatic hyperplasia since it reduces two of the parameters at the origin of the disease.

In another preferred embodiment, the daily dose of anethole trithione for the use thereof in the prevention and/or treatment of BPH is between 40 and 400 mg. Preferentially, this daily dose is between 80 and 240 mg.

In an even more preferred embodiment, the daily dose of anethole trithione is separated into two administrations of 20 to 200 mg each, even more preferentially into two administrations of 40 to 120 mg each.

By way of example, each administration may comprise 40, 50, 60, 70, 80, 90, 100, 110, 120, 150 or 200 mg of ATT.

In a preferred embodiment, the dose of anethole trithione is 80 mg per administration.

A fourth subject matter of the present disclosure relates to a pharmaceutical composition comprising a specific inhibitor of mitochondrial ROS production selected from ATT, ATX or an ATX ester or the combination of at least two of these molecules for preventing and/or treating BPH.

In a preferred embodiment, the composition comprises at least ATT.

In a particular embodiment, the composition comprises ATT and at least one other molecule selected from an alpha-reductase molecule, an alpha blocker molecule, and nicotinamide.

A composition of this type is suited to the therapeutic uses of the present disclosure, and can be administered, for example, orally or intravenously.

EXPERIMENTAL PART

Example 1: Preclinical Evaluation

ATT (anethole trithione) was administered to probasin-prolactin (Pb-PRL) mice. This is a transgenic mouse model in which prolactin is specifically overexpressed by the epithelial cells of the prostate, leading to development of benign hyperplasia having characteristics in common with the human pathology: tissue hypertrophy, hyperplasia of the epithelial and stromal cells, and intra-prostatic inflammation (Kindblom et al., 2003; Bernichtein et al., 2015a; Bernichtein et al., 2015b).

For the study, ATT was solubilized at a concentration of 15 mg/ml purified coconut oil and administered by gavage for 28 consecutive days at a once-daily dose of 60 mg/kg (or 4 ml/kg, equivalent to approximately 120-150 µl per mouse). The control group (excipient) was treated with the oil alone.

The dose adhered to for the study, 60 mg/kg, was thus selected because it made it possible to achieve, at time 10 hours, average ATC concentrations in plasma (153 ng/ml, n=6 mice) similar to those usually observed in humans in the 2-3 hours following the plasma peak after a single oral administration of 75 mg (or 1 mg/kg [He et al., 2001]), guaranteeing—in view of the very short half-life of the product in rodents (0.4 h in rats)—concentrations similar to what would be implemented in humans, at a reasonable dose, for at least half of a 24-hour cycle.

Each group included 12 Pb-PRL mice of average age 6±0.4 months.

I. Treatments and Harvest

Pb-PRL mice were accommodated in standard conditions (food ~20-22 kcal/day, 12 h day/night). The study was performed on mice of 5 to 6 months. The compound was administered daily by gavage for 28 consecutive days at a dose of 4 ml/kg. The weight of the animals was measured every week to evaluate the tolerance level. A decrease of 2 to 3 g of weight was observed in the mice as a result of the stress associated with the gavage.

Two experimental groups of 12 Pb-PRL mice were included in the study:

Group 1 (control group): excipient (purified coconut oil; 5 ml/kg).

Group 2 (ATT group); anethole trithione (60 mg/kg/day).

The animals were sacrificed at the end of the 28 days of treatment (cervical dislocation), and the prostates were harvested and analyzed by the standard procedures previously described in the literature (Bernichtein et al. Prostate 2015, Bernichtein et al. PLoS. ONE 2015, Bernichtein et al. Cancer Res 2017).

1. Study on the effect of ATT on the weight of the prostates of the Pb-PRL mice

The fresh weight of each prostatic lobe was measured upon sacrifice and normalized to the weight of the mouse. Likewise, the macroscopic features distinguishing the prostates of the ATT group of the control group were cataloged.

Figure 1B:
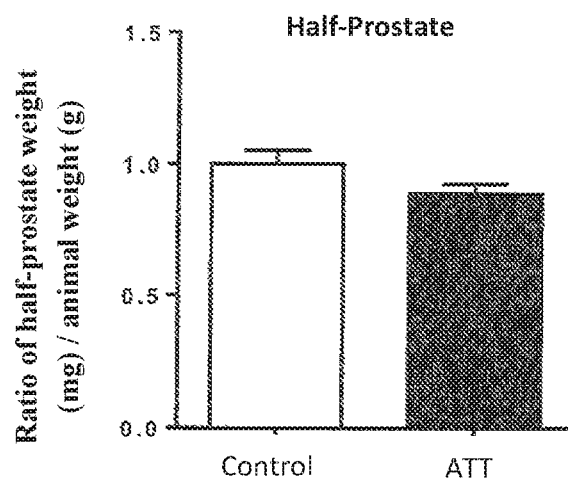
FIG. 1B shows the ratio between the weight of the half-prostate (in mg) and the weight of the animal (in g) for the control group and the ATT group.

The results on the lateral prostate and the half-prostate are shown in FIGS. 1a and 1b, respectively.

A tendency toward weight reduction in the prostate is noted, and is statistically significant in the lateral lobe.

2. Study on the effect of ATT on epithelial proliferation

Cell proliferation was measured by IHC Ki-67, which makes it possible to calculate the epithelium proliferation index (manual counting or Calopix software).

Figure 2:
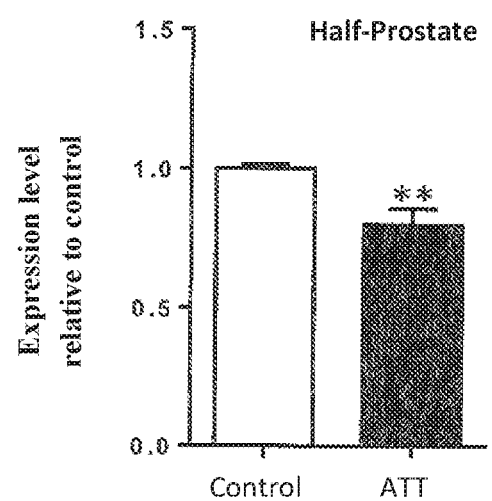
FIG. 2 shows the Ki-67 expression level observed in immunohistochemistry (IHC) for the control group and the ATT group.

The results of the analysis of the effect of ATT on epithelial proliferation on one half-prostate are presented in FIG. 2.

A statistically significant decrease in the epithelial proliferation of the prostate is noted, as estimated by factor Ki-67 immunohistochemistry (FIG. 2).

3. Study of the effect of ATT on the androgenic signal

This study was performed by RT-qPCR analysis of the expression of elements associated with androgenic signaling and of conventional targets of the androgen receptor in the prostate (AR, PSP 94, Srd5A1, Srd5A2) (Bernichtein et al. Prostate 2015, Sackmann Sala et al. J Pathol 2017).

Figure 3A:
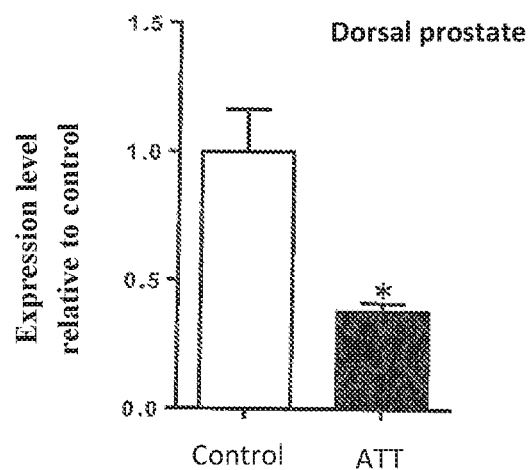
FIG. 3A shows the androgen receptor expression level observed in RT-qPCR in the dorsal prostate, for the control group and the ATT group.
Figure 3B:
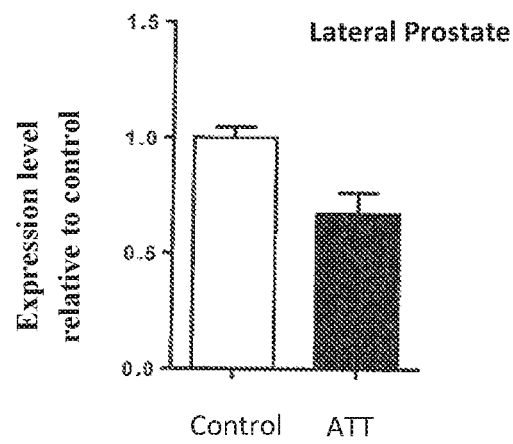
FIG. 3B shows the androgen receptor expression level observed in RT-qPCR in the lateral prostate, for the control group and the ATT group.
Figure 3C:
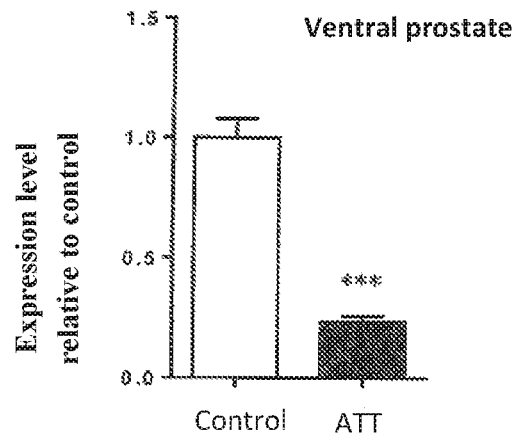
FIG. 3C shows the androgen receptor expression level observed in RT-qPCR in the ventral prostate, for the control group and the ATT group.
Figure 4A:
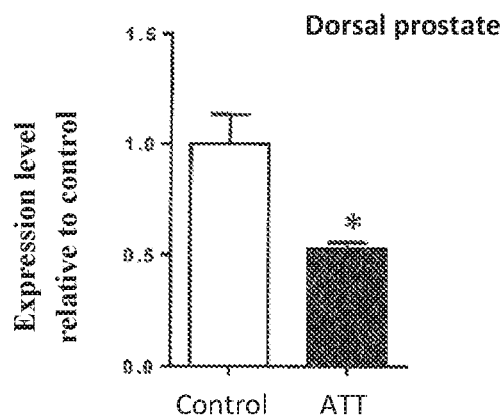
FIG. 4A shows the SRD5A1 receptor (5-alpha-reductase receptor) expression level observed in RT-qPCR in the dorsal prostate, for the control group and the ATT group.
Figure 4B:
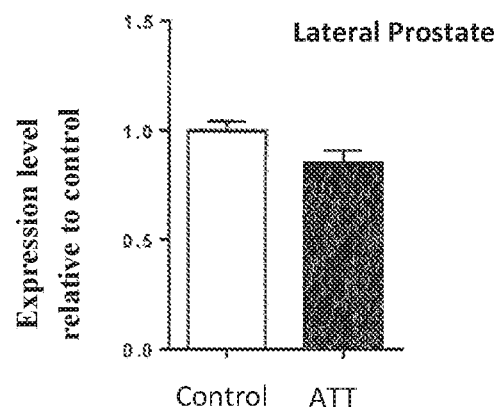
FIG. 4B shows the SRD5A1 receptor (5-alpha-reductase receptor) expression level observed in RT-qPCR in the lateral prostate, for the control group and the ATT group.
Figure 4C:
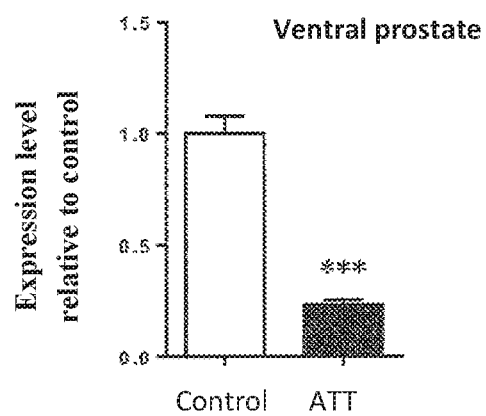
FIG. 4C shows the SRD5A1 receptor (5-alpha-reductase receptor) expression level observed in RT-qPCR in the ventral prostate, for the control group and the ATT group.
Figure 5A:
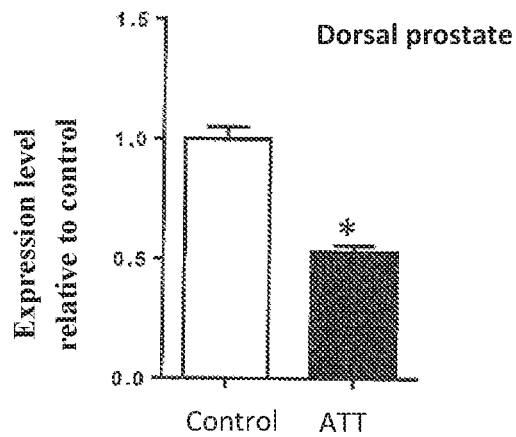
FIG. 5A shows the SRD5A2 receptor (5-alpha-reductase receptor) expression level observed in RT-qPCR in the dorsal prostate, for the control group and the ATT group.
Figure 5B:
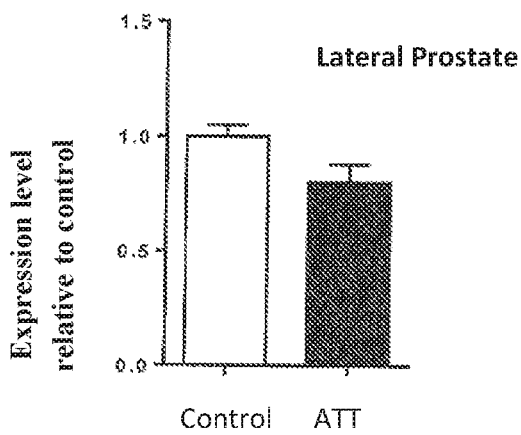
FIG. 5B shows the SRD5A2 receptor (5-alpha-reductase receptor) expression level observed in RT-qPCR in the lateral prostate, for the control group and the ATT group.
Figure 5C:
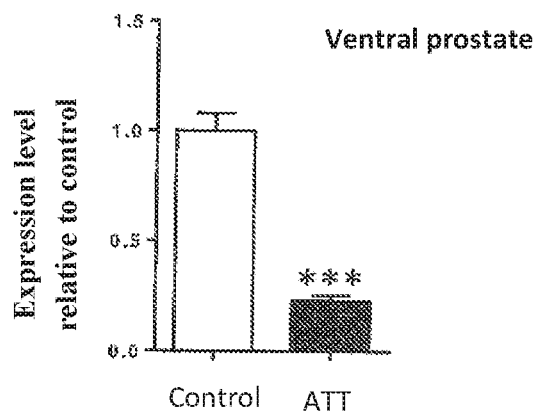
FIG. 5C shows the SRD5A2 receptor (5-alpha-reductase receptor) expression level observed in RT-qPCR in the ventral prostate, for the control group and the ATT group.
Figure 6A:
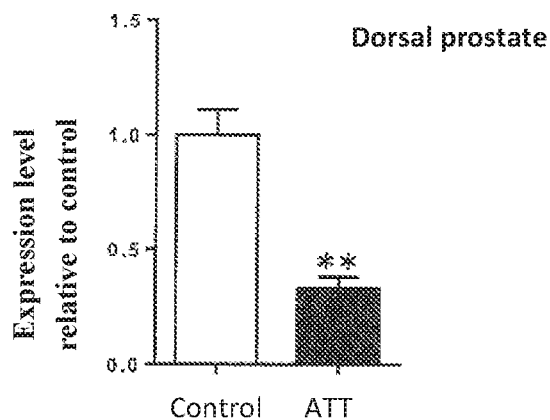
FIG. 6A shows the PSP94 (target gene activated via the androgenic pathway) receptor expression level observed in RT-qPCR in the dorsal prostate, for the control group and the ATT group.
Figure 6B:
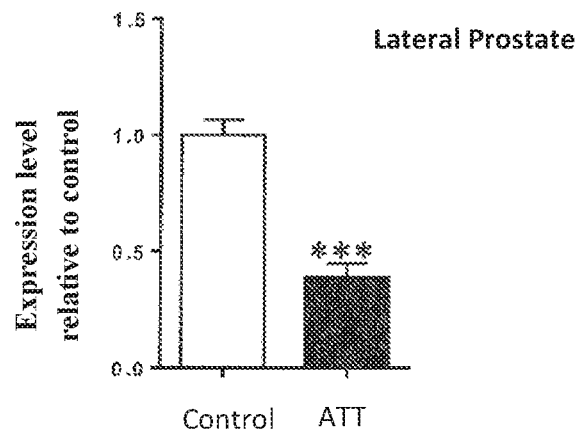
FIG. 6B shows the PSP94 (target gene activated via the androgenic pathway) expression level observed in RT-qPCR in the lateral prostate, for the control group and the ATT group.
Figure 6C:
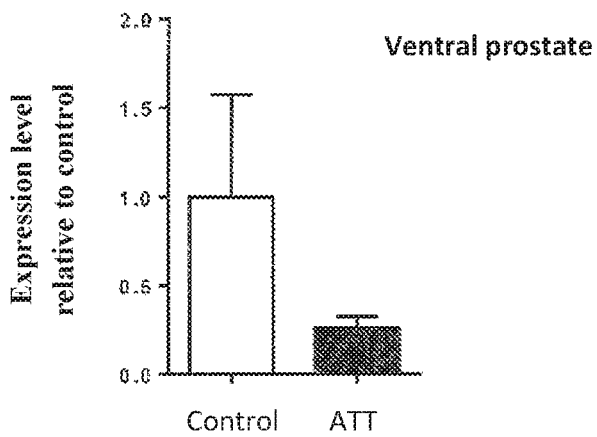
FIG. 6C shows the PSP94 (target gene activated via the androgenic pathway) expression level observed in RT-qPCR in the ventral prostate, for the control group and the ATT group.

The results of the analysis of the effect of ATT on the androgenic signal observable:

at the androgen receptor level of the dorsal, lateral and ventral prostate are presented in FIGS. 3A, 3B and 3C, respectively.

at the SRD5A1 (5-alpha-reductase) receptor level of the dorsal, lateral and ventral prostate are presented in FIGS. 4A, 4B and 4C, respectively.

at the SRD5A2 (5-alpha-reductase) receptor level of the dorsal, lateral and ventral prostate are presented in FIGS. 5A, 5B and 5C, respectively.

at the PSP94 receptor level of the dorsal, lateral and ventral prostate are presented in FIGS. 6A, 6B and 6C, respectively.

An anti-androgenic effect is observed, revealed by the statistically significant decrease in the expression of androgen receptor messenger RNAs, 5-alpha-reductase 1 and 2 enzymes (which transform testosterone into its active metabolite, dihydrotestosterone), and PSP94, a target gene activated via the androgenic pathway (Sackmann Sala et al., 2017).

4. Study on the effect of ATT on inflammation

The inflammation was measured using two approaches:

CD45 immunolabeling (IHC): making it possible to quantify the number and size of the inflammation sites (image analysis using Calopix software).

RT-qPCR of selected cytokines: IL6 and TNFa.

Figure 7:
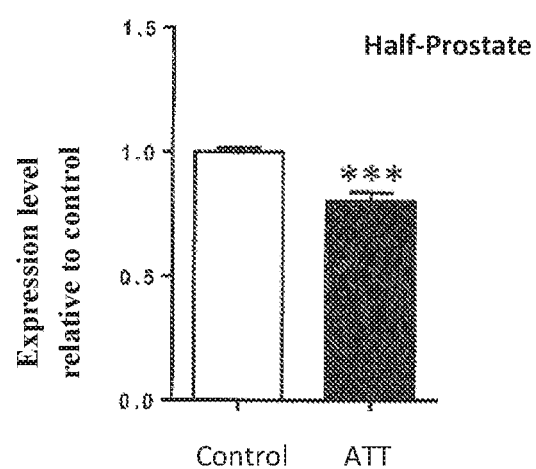
FIG. 7 shows the CD45 marker expression level observed by immune-marking on a half-prostate, for the control group and the ATT group.
Figure 8A:
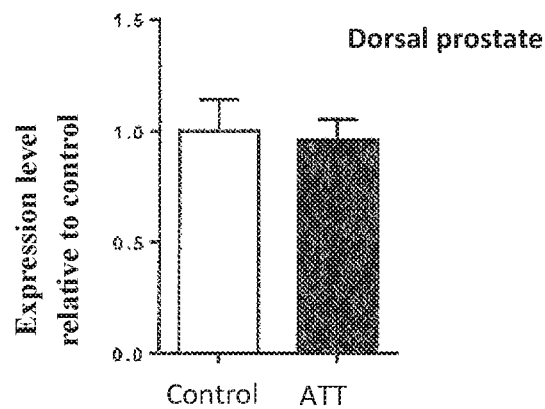
FIG. 8A shows the IL6 cytokine (inflammation marker) expression level observed in RT-qPCR in the dorsal prostate, for the control group and the ATT group.
Figure 8B:
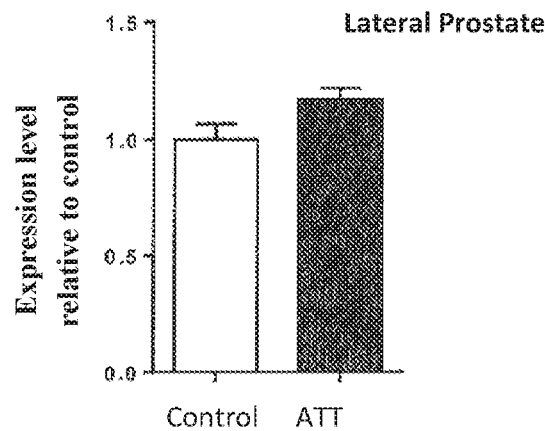
FIG. 8B shows the IL6 cytokine (inflammation marker) expression level observed in RT-qPCR in the lateral prostate, for the control group and the ATT group.
Figure 8C:
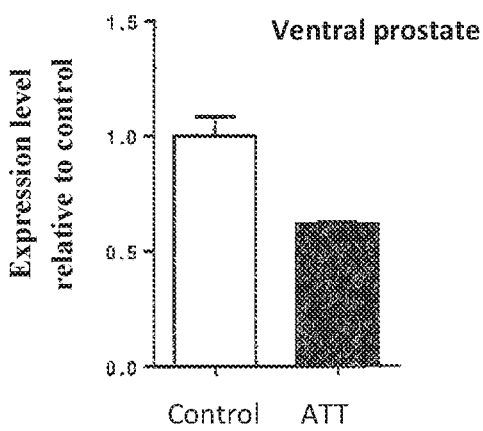
FIG. 8C shows the IL6 cytokine (inflammation marker) expression level observed in RT-qPCR in the ventral prostate, for the control group and the ATT group.
Figure 9A:
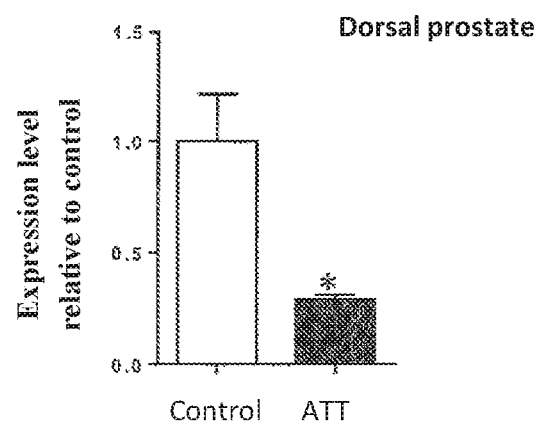
FIG. 9A shows the TNF alpha (inflammation marker) expression level observed in RT-qPCR in the dorsal prostate, for the control group and the ATT group.
Figure 9B:
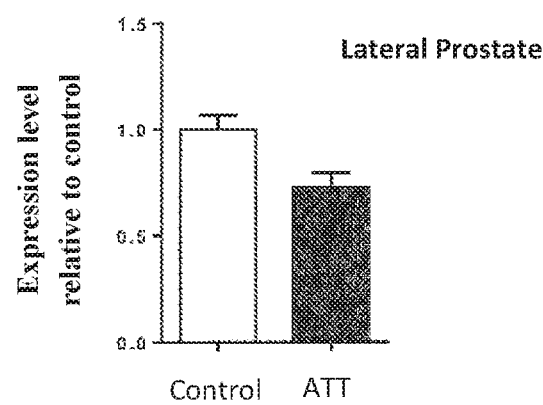
FIG. 9B shows the TNF alpha (inflammation marker) expression level observed in RT-qPCR in the lateral prostate, for the control group and the ATT group.
Figure 9C:
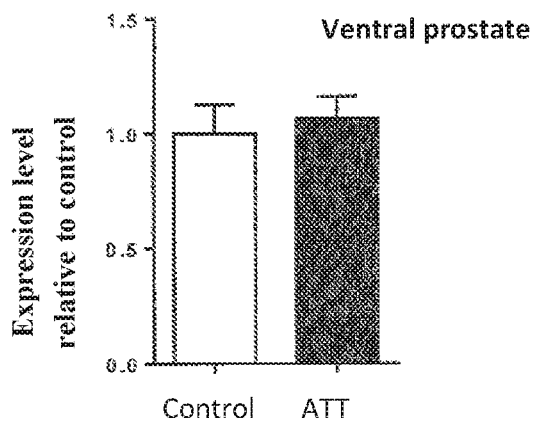
FIG. 9C shows the TNF alpha (inflammation marker) expression level observed in RT-qPCR in the ventral prostate, for the control group and the ATT group.

The results of the analysis of the effect of ATT on inflammation:

as visible by CD45 immunolabeling on a half-prostate are presented in FIG. 7.

as visible by IL6 RT-qPCR on the dorsal, lateral and ventral prostate are presented in FIGS. 8A, 8B and 8C, respectively.

as visible by TNFalpha RT-qPCR on the dorsal, lateral and ventral prostate are presented in FIGS. 9A, 9B and 9C, respectively.

A decrease in inflammation is observed, revealed by the statistically significant decrease in the number of positive leukocyte cell sites for the CD45 marker (Bernichtein et al., 2015a). This effect is supported by the decrease in the expression of some pro-inflammatory cytokines/receptors (IL6 and TNFalpha) and by the statistically significant increase in the scar fibrosis typically observed in this model upon a reduction in inflammation (Bernichtein et al., 2015a).

5. Study on the effect of ATT on oxidative stress

Oxidative stress will be measured using two approaches:

oxidation/carbonylation of the proteins by blot (Oxyblot™, Merck).

PHD1 and PHD3 dioxygenase expression (RT-qPCR).

Figure 10A:
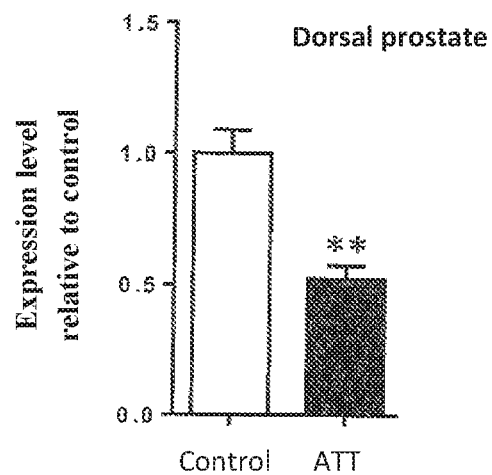
FIG. 10A shows the protein oxidation/carbonylation expression level observed by blot in the dorsal prostate, for the control group and the ATT group.
Figure 10B:
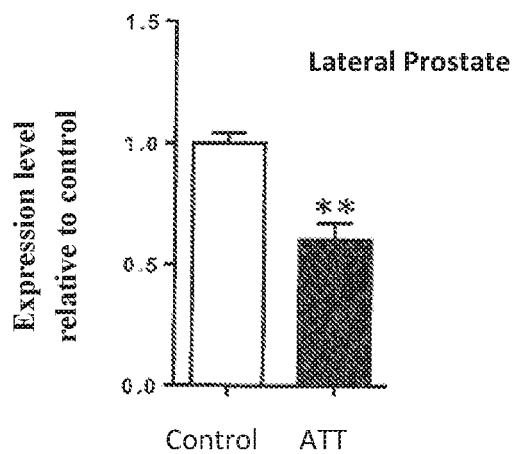
FIG. 10B shows the protein oxidation/carbonylation expression level observed by blot in the lateral prostate, for the control group and the ATT group.
Figure 10C:
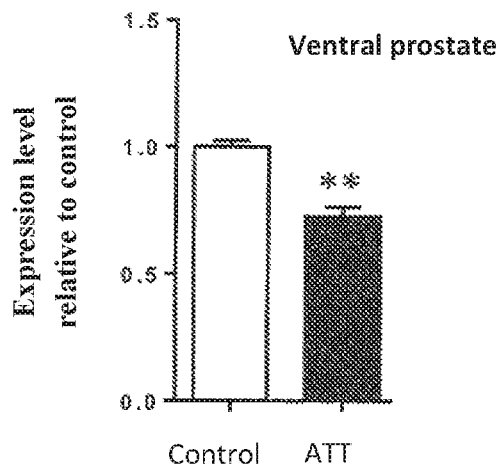
FIG. 10C shows the protein oxidation/carbonylation expression level observed by blot in the ventral prostate, for the control group and the ATT group.
Figure 11A:
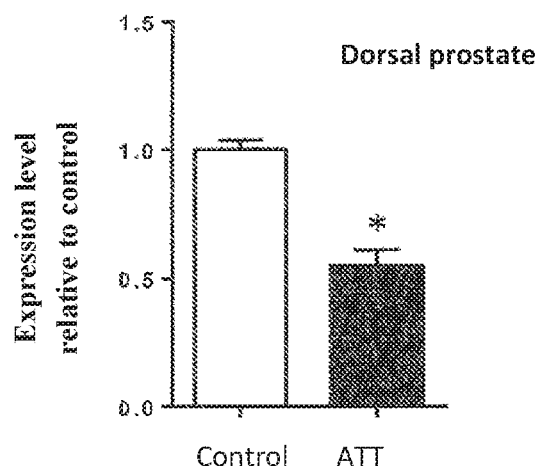
FIG. 11A shows the PHD1 dioxygenase (oxidative stress marker) expression level observed in RT-qPCR in the dorsal prostate, for the control group and the ATT group.
Figure 11B:
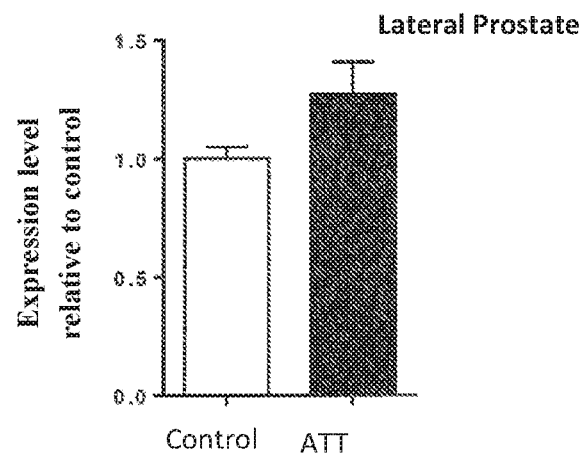
FIG. 11B shows the PHD1 dioxygenase (oxidative stress marker) expression level observed in RT-qPCR in the lateral prostate, for the control group and the ATT group.
Figure 11C:
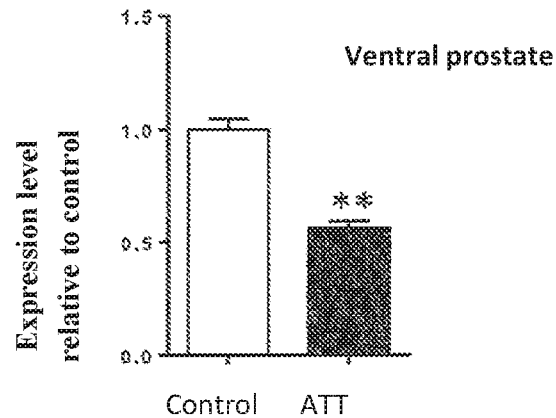
FIG. 11C shows the PHD1 dioxygenase (oxidative stress marker) expression level observed in RT-qPCR in the ventral prostate, for the control group and the ATT group.
Figure 12A:
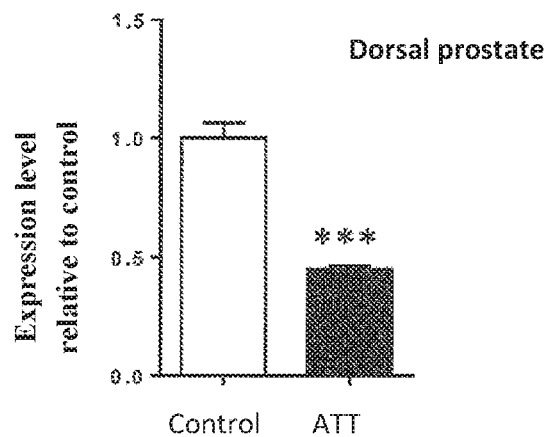
FIG. 12A shows the PHD3 dioxygenase (oxidative stress marker) expression level observed in RT-qPCR in the dorsal prostate, for the control group and the ATT group.
Figure 12B:
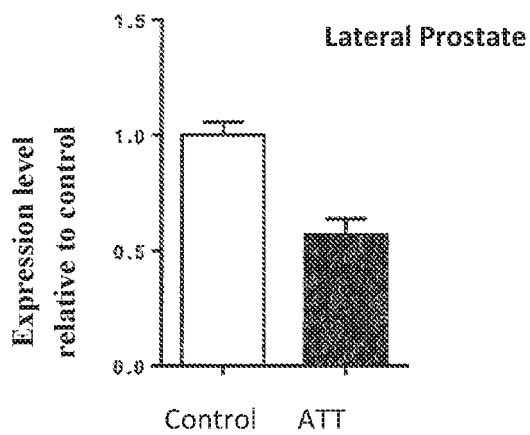
FIG. 12B shows the PHD3 dioxygenase (oxidative stress marker) expression level observed in RT-qPCR in the lateral prostate, for the control group and the ATT group.
Figure 12C:
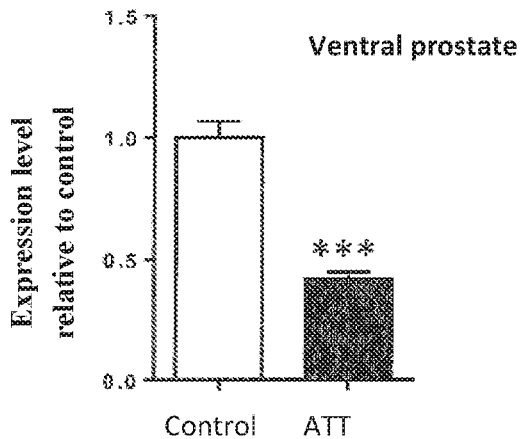
FIG. 12C shows the PHD3 dioxygenase (oxidative stress marker) expression level observed in RT-qPCR in the ventral prostate, for the control group and the ATT group.

The results of the analysis of the effect of ATT on oxidative stress:

observable by oxidation/carbonylation of the proteins by blot are presented for the dorsal, lateral and ventral prostate, respectively, in FIGS. 10A, 10B and 10C.

observable by PHD1 dioxygenase expression for the dorsal, lateral and ventral prostate are presented in FIGS. 11A, 11B and 11C, respectively.

as observable by PHD3 dioxygenase expression for the dorsal, lateral and ventral prostate are presented in FIGS. 12A, 12B and 12C, respectively.

A decrease in oxidative stress is observed, revealed by the statistically significant decrease in carbonylation of the proteins in all lobes (Oxyblot™ methodology) and in expression of the messenger RNAs of PHD1/PHD3 dioxygenase enzymes.

6. Study of the effect of ATT on hypoxia

Figure 13A:
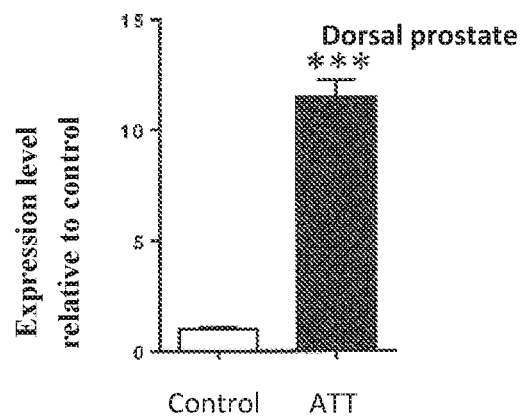
FIG. 13A shows the HIF1 alpha (hypoxia marker) expression level observed in RT-qPCR in the dorsal prostate, for the control group and the ATT group.
Figure 13B:
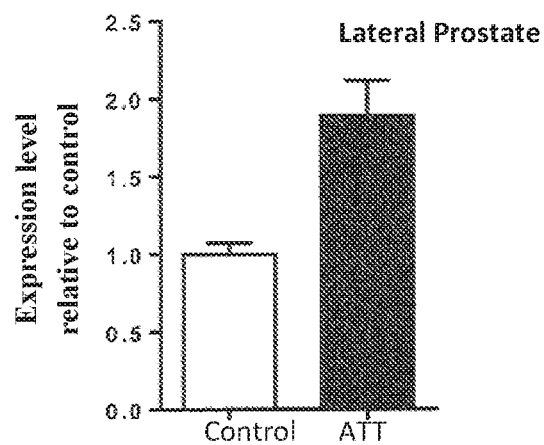
FIG. 13B shows the HIF1 alpha (hypoxia marker) expression level observed in RT-qPCR in the lateral prostate, for the control group and the ATT group.
Figure 13C:
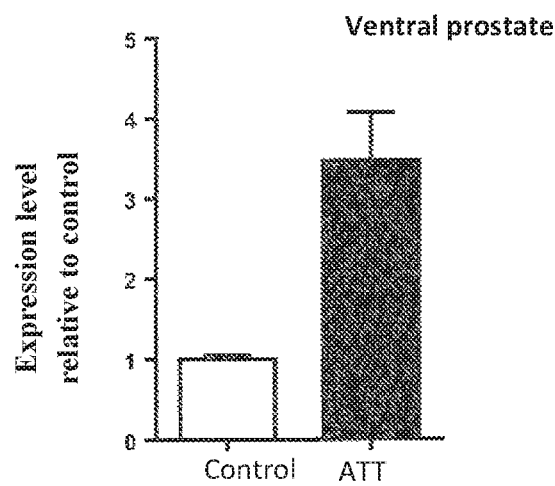
FIG. 13C shows the HIF1 alpha (hypoxia marker) expression level observed in RT-qPCR in the dorsal prostate, for the control group and the ATT group.

Hypoxia was observed by analysis of HIF1 alpha measured by RT-qPCR at the dorsal, lateral and ventral prostate. The results are presented in FIGS. 13A, 13B and 131C, respectively.

An increase in hypoxia is observed, revealed by the statistically significant increase, in one or more prostate lobes, in the expression of the messenger RNAs of the HIF1 alpha hypoxia marker.

II. Conclusion

The results of this preclinical study show that the ATT molecule has two desirable effects for effective treatment of benign prostatic hyperplasia: an anti-androgenic effect and an anti-inflammatory effect, in addition to the beneficial effect against oxidative stress.

It may be noted that, in this study, the mice were treated each day with a single dose sufficient for 12 hours. This was because of the risks associated with the stress involved in gavage for the animals.

Thus, the mice were only treated for 12 of 24 hours, and not for 24 of 24 hours as would be planned for humans, and this over a reduced period.

The results obtained are thus highly promising, since in spite of the short treatment duration and the treatment for 12 of 24 hours, good results were observed on the desired parameters for effective treatment of BPH.

Example 2: Clinical Evaluation

On a methodical point of view, the clinical improvement in a subject exhibiting BPH can be evaluated with reference to a scale that provides a consensus: the IPSS (International Prostate Symptom Score).

A study of this type can be performed over two time periods:
- over a short period of 2-3 months, tracking two elements as the main evaluation criterion: the clinical improvement and the PSA levels (if these have increased);
- over a long period of, for example, 2 years, evaluating the clinical symptoms and the progression rate of the disease in subjects who have become dissatisfied with their treatment using α1 blockers or 5-alpha-reductase. A study of this type may include three branches: branch 1: conventionally prescribed treatment used alone: α1 blockers or 5-alpha-reductase; branch 2: treatment with α1 blockers or 5-alpha-reductase+SULFARLEM® (or another inhibitor of mitochondrial ROS production, such as ATT); branch 3: SULFARLEM® (or another inhibitor of mitochondrial ROS production, such as ATT) used alone.

The invention claimed is:

1. A method of treating benign prostatic hyperplasia (BPH) in a subject, the method comprising administering to the subject anethole trithione (ATT) so as to treat the BPH.

2. The method of claim 1, wherein the administering to the subject is performed following chronic prostatitis.

3. The method of claim 1, wherein the ATT is administered in monotherapy.

4. The method of claim 1, further comprising administering to the subject the ATT at a daily dose between 40 mg and 400 mg.

5. The method of claim 4, comprising administering to the subject the ATT at a daily dose between 80 mg and 240 mg.

6. The method of claim 5, comprising administering to the subject the ATT at a daily dose of 80 mg.

7. A method of decreasing prostatic androgenic signal associated with benign prostatic hyperplasia (BPH) in a subject, the method comprising administering to the subject anethole trithione (ATT) so as to treat the BPH.

8. The method of claim 7, further comprising administering to the subject the ATT at a daily dose between 40 mg and 400 mg.

9. The method of claim 8, comprising administering to the subject the ATT at a daily dose between 80 mg and 240 mg.

10. The method of claim 9, comprising administering to the subject the ATT at a daily dose of 80 mg.

11. A method of inhibiting and/or decreasing prostatic inflammation associated with benign prostatic hyperplasia (BPH) in a subject, the method comprising administering to the subject anethole trithione (ATT) so as to treat the BPH.

12. The method of claim 11, further comprising administering to the subject the ATT at a daily dose between 40 mg and 400 mg.

13. The method of claim 12, comprising administering to the subject the ATT at a daily dose between 80 mg and 240 mg.

14. The method of claim 13, comprising administering to the subject the ATT at a daily dose of 80 mg per administration.

15. A method of decreasing prostatic androgenic signal and prostatic inflammation associated with benign prostatic hyperplasia (BPH) in a subject, the method comprising administering to the subject anethole trithione (ATT) so as to treat the BPH.

16. The method of claim 15, further comprising administering to the subject the ATT at a daily dose between 40 mg and 400 mg.

17. The method of claim 16, comprising administering to the subject the ATT at a daily dose between 80 mg and 240 mg.

18. The method of claim 17, comprising administering to the subject the ATT at a daily dose of 80 mg.

* * * * *